(12) United States Patent
Dondero

(10) Patent No.: US 6,708,340 B1
(45) Date of Patent: *Mar. 23, 2004

(54) APPARATUS AND METHOD RELATING TO A QUICK ATTACHMENT AND RELEASE GOGGLE MOUNTING SYSTEM

(75) Inventor: John Dondero, Ketchum, ID (US)

(73) Assignee: Eye Safety Systems, Inc., Sun Valley, ID (US)

( * ) Notice: Subject to any disclaimer, the term of this patent is extended or adjusted under 35 U.S.C. 154(b) by 271 days.

This patent is subject to a terminal disclaimer.

(21) Appl. No.: 09/715,245

(22) Filed: Nov. 17, 2000

Related U.S. Application Data

(63) Continuation-in-part of application No. 09/668,527, filed on Sep. 21, 2000, now Pat. No. 6,490,729.

(51) Int. Cl.$^7$ .................................................. A61F 9/00
(52) U.S. Cl. .................................................. 2/10; 2/63
(58) Field of Search ................ 2/5, 422, 10, 6.2, 2/6.3, 425; 128/201.24

(56) References Cited

U.S. PATENT DOCUMENTS

| | | | | |
|---|---|---|---|---|
| 4,686,712 A | | 8/1987 | Spiva ............................ 2/10 |
| 4,796,308 A | * | 1/1989 | Bourgeois ........................ 2/10 |
| 5,291,880 A | * | 3/1994 | Almovist et al. ...... 128/201.22 |
| 5,347,655 A | * | 9/1994 | Garrett ............................ 2/10 |
| 5,940,891 A | | 8/1999 | Lane ............................. 2/426 |
| 6,490,729 B1 | * | 12/2002 | Dondero ........................ 2/10 |

\* cited by examiner

*Primary Examiner*—Katherine Moran
(74) *Attorney, Agent, or Firm*—Graybeal Jackson Haley LLP

(57) ABSTRACT

System and methods for mounting a goggle to a helmet. The systems comprising a retaining post. The retaining post has a distal portion that has a portion with a greater cross section than the remainder of the retaining post. The retaining post may be fastened to a helmet brim by a screw type fastener. The portion having a greater cross section may be a resilient serrated washer secured to an end of the retaining post. The system further comprises a strap is provided with a first end that is attachable to a goggle and a second end with an opening therein. The opening is sized to pass interferingly over the greater cross section portion of the distal portion of the retaining post.

25 Claims, 3 Drawing Sheets

APPARATUS AND METHOD RELATING TO A QUICK ATTACHMENT AND RELEASE GOGGLE MOUNTING SYSTEM

RELATION TO PREVIOUS APPLICATION

This application is a continuation-in-part of application Ser No. 09/668,527 filed on Sep. 21, 2000, now U.S. Pat. No. 6,490,729.

TECHNICAL FIELD

The present invention relates to quickly attaching a goggle to and releasing a goggle from a helmet.

BACKGROUND

Goggles have been available in the market place for many years. Goggles can be attached to a user's headwear such as a fireman's or construction worker's helmet. Other goggles are used by sports enthusiasts such as motorcycle riders, pilots, skydivers and skiers.

For some uses, such as a prolonged activity like skiing, a goggle can be attached to and detached from the helmet at the leisure of the user. Since the user knows when a particular activity will begin, and knows that he or she will most likely wear the goggles throughout the duration of the event or activity, the need for a quickly attachable and releasable goggle is minimal.

For other uses, such as fighting fires, there is a need to quickly attach and release the goggles, often when the user is busy doing something else and has only one hand free. Some previous mounting systems have required two hands to join two mating parts together. Some other systems require the dexterity of an un-gloved hand to attach or release the goggle from the helmet. In emergency scenarios, removing one's gloves can be a waste of precious time, or dangerous if in the vicinity of sharp or burning objects. Also, a goggle is often desired as eye protection by fire fighters and rescue personnel because a face shield alone does not provide the level of eye protection required in an environment filled with smoke or airborne debris.

Therefore, there is a need for a goggle mounting system that permits quick attachment to and release of a goggle from the helmet with one hand and while wearing gloves.

SUMMARY OF THE INVENTION

The present invention provides system, and methods for quickly attaching a goggle to a helmet and releasing the goggle from the helmet. Such systems and methods are desirable in activities of uncertain duration or which may involve abrupt changes in the type of activity or physical environment, such as fire fighting and emergency rescue. The present invention is simple to use, can be used with a helmet having a face shield, and can be readily used by someone wearing gloves. It also permits quick and simple assembly during manufacture of the helmet or field retrofit.

In one aspect of the invention a goggle mounting system is provided comprising a retaining post that is mounted directly to a section of helmet, such as the brim. The retaining post has a portion that is of a greater cross section that the remainder of the post. A strap that is attachable to a goggle at one end has an opening in the other end, such as a grommet. The grommet is sized to pass interferingly over the greater cross section portion of the retaining post. The greater cross section portion may be a resilient member, such as a serrated plastic washer, that deforms upon passage of the grommet over it, or conversely, in an alternative embodiment, the greater cross section portion may be comprised of a relatively inflexible material, such as a plastic bead, and the grommet would be comprised of a resilient material so that it can deform, or stretch, upon passage over it. The post is mounted to the helmet by a variety of well known fasteners.

A particular embodiment of the invention comprises a substantially cylindrical retaining post with a substantially axial hole through it. A resilient washer, such as a serrated washer, is mounted to one end of the retaining post by a fastener. The same fastener may be sued to secure the retaining post to the helmet, or a second fastener may be used to secure the retaining post.

Another aspect of the invention is the combination of the retaining post and strap described above, and a goggle. A further embodiment includes a helmet.

DETAILED DESCRIPTION OF THE INVENTION

The present invention provides a system and method for quickly attaching a goggle to a helmet and removing a goggle from the helmet. The invention will be described principally as it applies to a type of helmet commonly worn by fire fighters and emergency rescue personnel. However, it is useable on a wide variety of helmets, preferably with a brim, but as will be discussed below, the system is adaptable to brim-less helmets as well. The invention is advantageous because it permits a user to easily and quickly secure his or her goggles to the helmet and to easily and quickly detach the goggles from the helmet, even if the user is wearing gloves or if the helmet has a face shield.

Figure 1A:
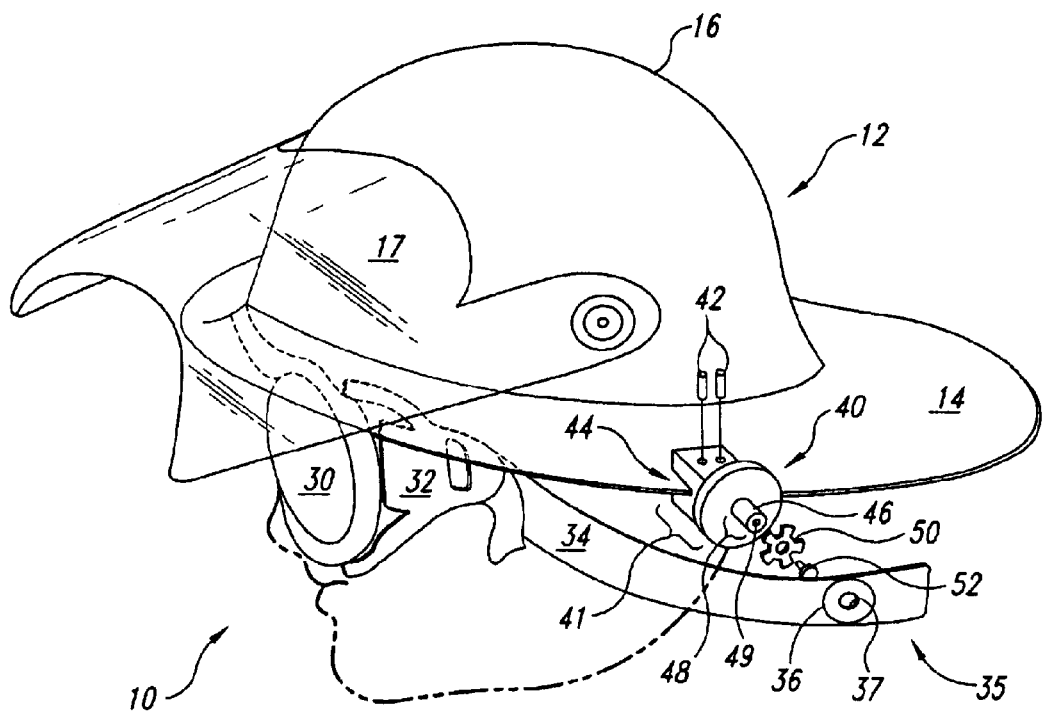
FIG. 1A is an view of the goggle mounting system in use on a firefighter's helmet, which shows in part an exploded view of a bracket body.
Figure 1B:
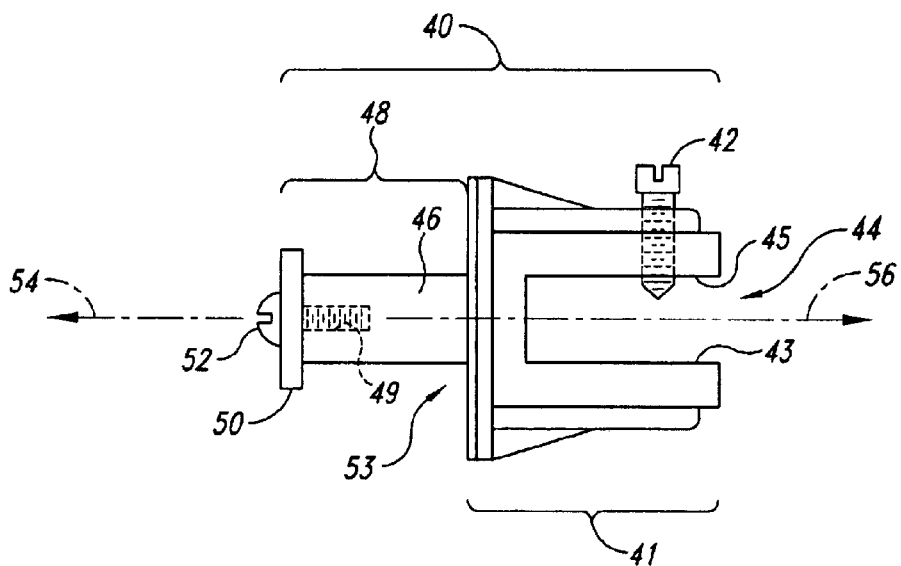
FIG. 1B is a side view of the bracket body depicted in FIG. 1A.

Referring to FIGS. 1A and 1B, FIG. 1A shows one embodiment of the present invention in use with a fireman's helmet, while FIG. 1B shows a side view of the bracket body of this embodiment shown in FIG. 1A. In FIG. 1A, a fire fighter 10 is shown wearing a helmet 12. The helmet has a brim 14 surrounding the crown 16. Mounted to the crown 16 is a face shield 17 which can be pivoted downward as desired. The fire fighter 10 is wearing a goggle 30 attached to a strap 34. The strap has a first strap end 32 that is adapted for attachment to the goggle 30. The second strap end 35 includes a grommet 36 with an opening 37. The strap 34 is attached to a bracket body 40 by passing the grommet 36 over a resilient washer 50 onto a retaining post 46. The sizes of the opening 37 and the resilient washer 50 are chosen so that there is relative interfering passage of the two elements when the goggle is attached or released.

A bracket body 40 is shown mounted to helmet brim 14. The bracket body 40 is the entire structure that is mounted to the helmet and to which the strap 34 is attached. The bracket body 40 includes a retaining post 46 which extends in a first direction 54. The first direction 54 generally points away from the helmet when the bracket body 40 is installed on the helmet brim 14. The retaining post 46 has a distal portion 48 with a hole 49 therein. By definition, the distal portion includes a portion of the retaining post 46 displaced from the base end 53 of the retaining post 46 where its base end 53 joins a mounting bracket 41. A resilient serrated washer 50 is fastened to the retaining post 46 by screw 52. The mounting bracket 41, which extends in a second direction 56, generally points towards the helmet. The mounting bracket 41 has a slot 44 establishing a first slot wall 45 and a second slot wall 43. The slot 44 receives a portion of the helmet brim 14 between the slot walls 45 and 43 and is secured to the brim by tightening set screws 42 which pass through the mounting bracket 41 and the first slot wall 45. The tightening of the set screws 42 essentially clamps the brim 14 between the set screws 42 and the second slot wall 43. An identical bracket body can be attached to the brim 14 on the other side of the helmet 12, but is not shown in this view. The bracket body 40 can be constructed of a molded plastic material. Other materials and forming methods are useful to form such a bracket such as metal machining or casting.

When a fire fighter needs to use the goggle, he simply pushes the grommet opening 37 over the resilient serrated washer 50. The grommet opening 37 and the washer 50 are sized to permit interfering passage of the washer 50 and the grommet 36. "Interfering passage" refers to the relative displacement of the washer 50 and the grommet 36, wherein the largest cross section dimension of the washer 50 is smaller than the opening 37 in the grommet 36. The dimensional differences causes there to be interference between the washer 50 and the grommet 36. However, the inherent resiliency of the washer 50 allows it to deform sufficiently to permit passage of the grommet 36.

The primary tension in the strap 34 is approximately perpendicular to the axis of the post, so it is not necessary for the strap to be fixed in place by some other means that may require greater effort, dexterity, or two hands to attach the strap 34 to the bracket body 40. When the fire fighter is ready to remove the goggle, he simply grasps the strap 34 near the grommet 36 and pulls generally outwardly or away from the brim 14; essentially in the same direction as first direction 54. There is no need for any substantial displacement of the grommet 36 perpendicular to the first direction 54. Therefore, the strap 34 can be attached or removed in a single smooth motion.

The bracket body 40 can be attached to the helmet 12 at any place along the brim 14 that suits the wearer of the helmet by simply tightening the set screws 42. As long as the retaining post 46 generally points sideways away from the helmet or somewhat rearwardly and/or upwardly the system will retain the goggle until the wearer pulls the grommet 34 off the post 46. If the bracket body 40 were mounted so that the retaining post 46 pointed somewhat towards the front of the helmet, the interference of the grommet 36 and the resilient washer 50 will still hold the grommet 36 in place unless the tension in the strap is high enough to overcome the resistance presented by the interfering fit of the grommet 36 and the resilient washer 50.

The resilient washer 50 does not need to be a washer of the serrated type shown. The resilient washer 50 may be replaced by any resilient member or device that, when incorporated as part of the bracket body, either by unitary formation or later attachment, serves the function of permitting interfering passage of the grommet 36. The resilient member may be a protrusion formed as part of the post or attached to it as by the screw 52, glue, or other method of attachment. The resilient washer, or other resilient member, establishes a portion of the retaining post 46 having a greater cross section than the remainder of the retaining post 46. This greater cross section portion, which in the case of this embodiment is resilient washer 50, need not be at the very end of retaining post 46 as shown in FIG. 1B. It could be anywhere along the length of the distal portion 48 sufficient to allow passage of the grommet 36 past it and still permit the grommet to seat along the remainder of the retaining post 46 where the cross section is approximately equal to or smaller than the size of the opening 37.

The greater cross section portion of the retaining post 46 can also be a non-resilient material or device, and the grommet of a resilient material, wherein the sizing of the respective elements still permits interfering relative passage. For example, the greater cross section portion may simply be a sphere-like shape molded on the end of the retaining post 46. The grommet can be comprised of a resilient material, such as plastic, that will stretch or deform enough to pass over the bead. In another variation, both the grommet and the greater cross section portion may be comprised of relatively resilient material so that both elements deform upon passage of the grommet over the distal portion of the retaining post. Additionally, the grommet may be replaced by a shape or device having sufficient resiliency or flexibility to deform when forced over the distal portion 48 of the retaining post 46. An alternative to the grommet shown can be as simple as a reinforced hole, much like a button hole, sewn into the second strap end 35, or a planar plastic tab mounted at the second strap end 35 that has a slit or other passage through it that will permit relative interfering passage of the greater cross section portion of the retaining post 46. In yet another variation, a hook-like structure can be mounted at the second strap 35 end that will pass around the retaining post, but is sized to not permit it to slide past the part of the retaining post including the greater cross section, namely, the distal portion. Another device that can serve the same function as a hook, is a hoop-like fastener of the type commonly use on the straps of a workman's coveralls to hook onto a button at the front of the coveralls.

Figure 2A:
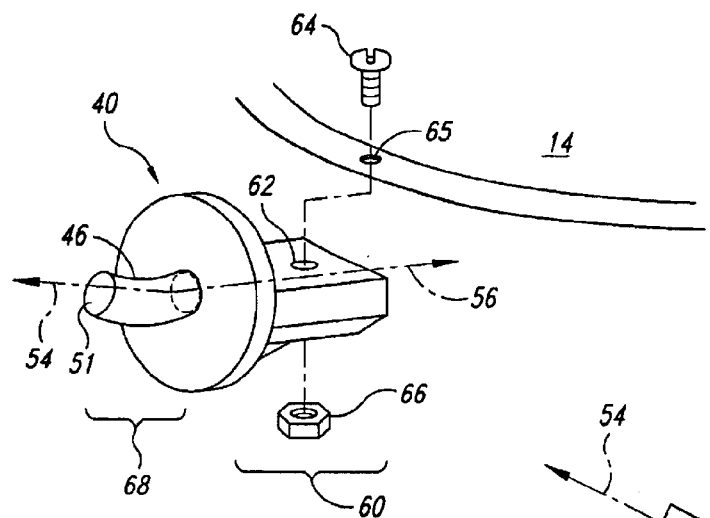
FIG. 2A is a perspective view of an alternative embodiment of the bracket body depicting a curved retaining post and a mounting stud.
Figure 2B:
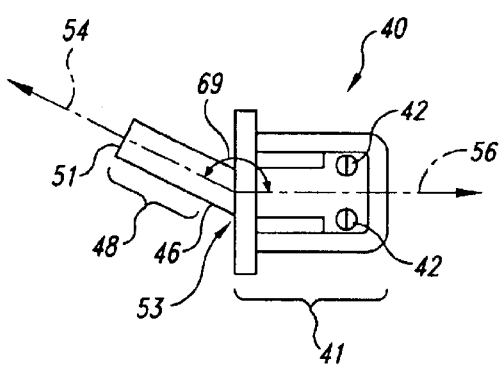
FIG. 2B is a top view of the bracket body depicted in FIG. 2A.

Referring to FIG. 2A, an alternative embodiment of the bracket body 40 is depicted. In this embodiment, the bracket body 40 does not have a mounting bracket 41 or a slot 44 as described previously. Instead, it is has a mounting stud 60 with a hole 62 through it. This configuration of bracket body 40 can be mounted to a brim by passing a fastener, such as screw 64, through an appropriately sized hole 65 in the helmet brim 14 and hole 62, then tightening nut 66 to secure the assembly. In this embodiment, as shown in FIG. 2A, the retaining post 46 can be bent or curved along a portion of its axial length 68 in a manner so that when it is attached to the brim 14, the retaining post 46 curves generally rearwardly and/or upwardly. The length of the curved portion of the retaining post 46 can vary, and it may incorporate the full length of the retaining post 46. The net effect of curving the post is to re-define the first direction 54. As indicated in FIG. 2B, the first direction 54 originates at the base 53 of the retaining post 46 and runs out through the extreme distal end 51 of the retaining post 46. Accordingly, an angle 69 is formed between the first direction 54 and the second direction 56. In this approach, having a resilient member, such as washer 50, is not necessary. The grommet opening 37 can be sized to freely pass over the distal portion 48. The strap 34 will tend to stay in place when the grommet 36 (not shown) is placed on the post, because of the tension in the strap 34, until removed by an outward force, with a nominal rearward and/or upward component, applied to the strap 34 to remove the grommet 36 from the curved retaining post 46.

As shown in FIG. 2B, an alternative to curving the retaining post is to simply set the retaining post 46 at an angle 69 that is substantially less than 180 degrees relative to the mounting bracket 41 as defined by the first direction 54, and the second direction 56, such that the retaining post 46 is disposed generally rearwards and/or upwardly (i.e., away from the direction of the tension force imparted by strap 34). (Also, note that the bracket body 40 shown in FIG. 2B includes mounting bracket 41 instead of mounting stud 60 shown in FIG. 2A. However, the two different structures for mounting the bracket body 40 to the helmet can be interchanged with the various retaining post configurations.) In this way the retaining post can achieve a generally rearward and/or upward angle and retain the strap in much the same manner as discussed previously in relation to the curved retaining post embodiment. Of course the angle between the first direction 54 and second direction 56 can be essentially equal to 180 degrees and the bracket body can be canted slightly during installation to achieve a somewhat rearward pointing retaining post to again retain the strap as just discussed. It should be noted that a single bracket body formed with an angle of less than 180 degrees between the first direction 54 and the second direction 56 would result in an asymmetrical installation unless a mirror image bracket body were formed. In other words, mirror image, or left and right hand, bracket bodies, might be used depending on the method of mounting to the helmet and any requirement that the installation be symmetrical. Likewise, depending on how the straps are adapted to attach to the goggle, there may be a requirement for mirror image straps.

Figure 3:
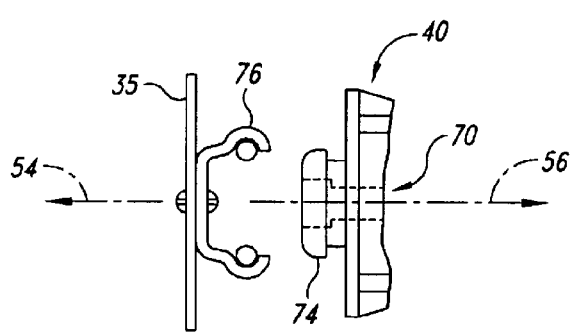
FIG. 3 is a side view of another alternative embodiment of the bracket body depicting a bracket body with a snap member thereon, the bracket body being adaptable to flush mount to the side of a helmet without a brim.

Another alternative embodiment is shown in FIG. 3. This arrangement has the advantage of being mountable to a helmet without a brim. A hole 70 through the center of bracket body 40 is used for attachment to the helmet crown 16 (helmet not shown) by a fastener such as a screw, rivet or glue. The bracket body 40 does not include a mounting bracket 41 or a mounting stud 60 as described above. Instead of employing a retaining post and grommet configuration as described above, this embodiment utilizes a first snap member 74 and a second snap member 76. First snap member 74 extends in the first direction 54 and is either attached to the bracket body 40 or formed as an integral part of the bracket body 40. The mating second snap member 76 is attached to the second strap end 35. The mating snap members can be of a variety of well known devices for accomplishing this type of function. Other mounting methods such as using mounting bracket 41 or mounting stud 60 as discussed above and shown in FIGS. 1A and 2A would work in this embodiment for use on brimmed helmets.

Figure 4:
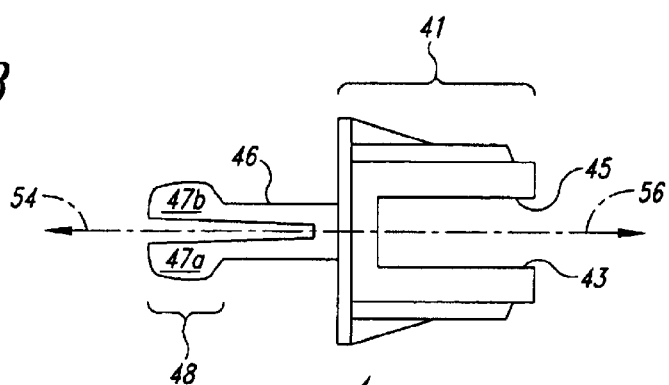
FIG. 4 is perspective view of another embodiment of the bracket body depicting a slotted retaining post with flexible fingers.

Yet another embodiment is shown in FIG. 4. In this embodiment, the retaining post 46 is separated along a portion of its length substantially parallel to its axis. Two fingers 47a and 47b are thus formed. The distal portion 48 of the retaining post 46 is sized to interfere with passage of the grommet 36 (not shown) over the distal portion 48. The fingers 47a and 47b are designed to flex substantially towards each other to the extent necessary to allow passage of the grommet 36 over the distal portion 48. Other variations of this approach are possible that might include more than two fingers.

Figure 5A:
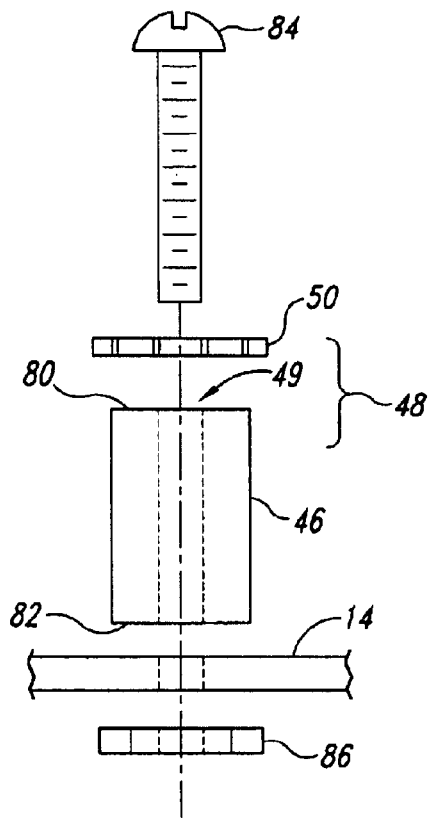
FIG. 5A is an exploded side view of another embodiment of a retaining post shown mounted directly to a section of a helmet.

FIG. 5A depicts an embodiment comprising retaining post 46 and its associated structures wherein the retaining post 46 is directly mounted onto the helmet. The hole 49 passes through the retaining post 46 substantially in an axial direction from a first post end 80 to a second post end 82. The first fastener 84, such as a machine screw, is of a length sufficient to pass through the resilient member 50, such as a serrated washer comprised of a flexible material, through the retaining post 46, through a section of brim 14 where it is then engaged by a second fastener 86, such as a nut. The entire assembly is secured by tightening the fasteners 84 and 86.

Figure 5B:
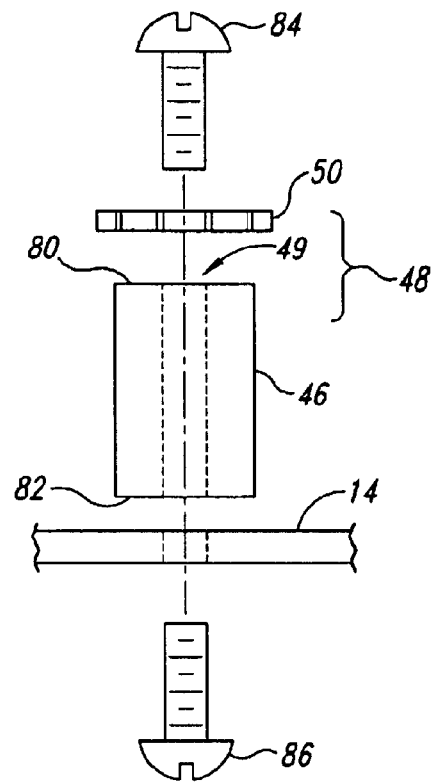
FIG. 5B is a an exploded side view of the retaining post of FIG. 5a employing an alternative mounting method.

FIG. 5B is a variation on the embodiment depicted in FIG. 5a. In this embodiment the first fastener 84 is used just to fasten resilient member 50 to first post end 80. The first fastener 84 is of a type that will frictionally engage the material of retaining post 46 surrounding hole 49, thus securing the resilient member 50 to the first post end 80. The second fastener 86 is used to secure the retaining post 46 to a section of the brim 14 by frictional engagement of the second fastener 86 with the material of the retaining post 46 surrounding hole 49 at a second post end 82. The fasteners 84 and 86 may be screws bearing threads designed to engage a softer material much like a wood screw is designed to frictionally engage wood. Such a choice of fasteners also allows for releasing the retaining post 46 from the brim 14 if replacement or repair is required. The fasteners could also be of a type that are not intended for removal, such as a bonded rivet. The resilient member 50 can be fastened to the first post end 80 by some other means, such as an adhesive, or it can be formed as an integral part of the retaining post 46 such as by a plastic molding process. Also, the hole 49 need not pass completely through the retaining post 46. Although not shown, there may be two or more holes passing substantially axially part way into the retaining post from the ends 80 and 82.

Figure 5C:
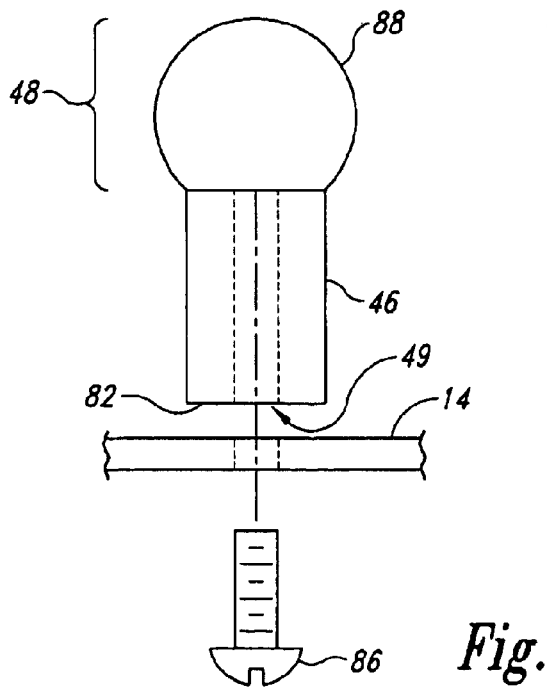
FIG. 5C is an exploded side view of the retaining post showing an alternative structure for aiding in retaining a goggle strap thereon.

FIG. 5C depicts another embodiment wherein the retaining post 46 bears on the distal portion 48 a bead 88. The bead 88 may formed as an integral part of retaining post 46. Alternatively, the bead 88 could be a separate element with a hole passing through it and maybe secured in place by a fastener much like the resilient member 50 as described above in relation to FIG. 5A. In this embodiment the bead 88 may not necessarily be comprised of a resilient material. In such a configuration, the opening 37 in the strap 34 is designed to deform when passing over the bead 88. For instance, a grommet 36 may be selected from a material having flexible or deformable properties so it can stretch sufficiently to pass over the bead 88.

The method of use of the systems described above is quite simple. Once the user retrieves the goggles from a storage location, such as a coat pocket or a pouch on an equipment belt, the user simply grasps either of the two straps 34 at or near the strap end 35. The user then pushes the grommet 36, or equivalent opening, past the resilient washer 50, or its equivalent structures, into a seated position on the retaining post 46. The user then grasps the other strap 34, positions the goggles over their eyes and repeats the attachment step described above. The removal of the goggles is essentially the reverse of the previous discussion. Again, as described previously, some small amount of rearward and/or upwardly force may be required in addition to an outwardly directed removal force if the retaining post is pointed rearwardly and/or upwardly to some degree. Similar forces and motions may be required if the embodiments incorporating snap members, or other hook-like or hoop-like devices, or their equivalents, are employed as described above.

It will be apparent to those skilled in the art, that the systems and methods for retaining the strap upon the retaining post and bracket mounting approaches disclosed above may be combined to create embodiments not specifically described or shown in the drawings.

The terms set forth in this application are not to be interpreted in the claims as indicating a "means plus function" relationship unless the word "means" is specifically recited in a claim, and are to be interpreted in the claims as indicating a "means plus function" relationship where the word "means" is specifically recited in a claim. The term "having" in the claims is to be interpreted as meaning the claim may include additional elements that are not specifically recited in the claim.

It is to be understood that even though various embodiments and advantages of the present invention have been set forth in the foregoing description, the above disclosure is illustrative only, and changes may be made in detail, and yet remain within the broad principles of the invention. Therefore, the present invention is to be limited only by the appended claims.

I claim:

1. A goggle mounting system for quickly mounting a goggle to and releasing a goggle from a helmet, the system comprising:
   a retaining post capable of being directly mounted to the helmet, the retaining post configured to releasably engage a goggle and further having a greater cross section portion at a distal portion of the retaining post; and
   a strap having a first strap end able to attach to a goggle, and a second strap end having an opening therein, the opening being sized to pass interferingly over the greater cross section portion of the retaining post.

2. The goggle mounting system of claim 1, wherein the opening is resilient.

3. The goggle mounting system of claim 1, wherein the greater cross section portion of the retaining post comprises a resilient member attached to the retaining post.

4. The goggle mounting system of claim 3, wherein the resilient member is a serrated washer.

5. A goggle mounting system for quickly mounting a goggle to and releasing a goggle from a helmet, the system comprising:
   a retaining post capable of being directly mounted to the helmet, the retaining post further having a greater cross section portion at a distal portion of the retaining post; and
   a strap having a first strap end able to attach to a goggle, and a second strap end having an opening therein, the opening being sized to pass interferingly over the greater cross section portion of the retaining post, wherein the opening is a grommet.

6. The goggle mounting system of claim 5, wherein the retaining post is configured to releasably engage the goggle.

7. A goggle mounting system for quickly mounting a goggle to and releasing a goggle from a helmet, the system comprising:
   a retaining post capable of being directly mounted to the helmet, the retaining post further having a greater cross section portion at a distal portion of the retaining post; and
   a strap having a first strap end able to attach to a goggle, and a second strap end having an opening therein, the opening being sized to pass interferingly over the greater cross section portion of the retaining post, wherein the opening is a grommet comprised of a resilient material.

8. The goggle mounting system of claim 7, wherein the retaining post is configured to releasably engage the goggle.

9. A goggle mounting system for quickly mounting a goggle to and releasing a goggle from a helmet, the system comprising:
   a retaining post capable of being directly mounted to the helmet, the retaining post further having a greater cross section portion at a distal portion of the retaining post; and
   a strap having a first strap end able to attach to a goggle, and a second strap end having an opening therein, the opening being sized to pass interferingly over the greater cross section portion of the retaining post, wherein the retaining post is releasable from the helmet.

10. The goggle mounting system of claim 9, wherein the retaining post is configured to releasably engage the goggle.

11. A goggle mounting system for quickly mounting a goggle to and releasing a goggle from a helmet, the system comprising:
    a retaining post capable of being directly mounted to a helmet and having a resilient member mounted to a distal portion of the retaining post,
    at least one fastener passing into the retaining post in a generally axial direction for mounting the retaining post to a helmet; and
    a strap having a first strap end able to attach a goggle, and the strap having a second strap end having an opening therein, which is sized to pass interferingly over the resilient member.

12. The system of claim 11, wherein the resilient member is a washer.

13. The system of claim 12, wherein the washer is a serrated washer.

14. The system of claim 11, wherein the retaining post is configured to releasably engage the goggle.

15. A goggle system retaining post for attachment to a helmet, the retaining post comprising:
    a retaining post having a first post end, a second post end and at least one substantially axial hole therethrough;
    a resilient member mounted to the first post end; and
    the retaining post being directly mountable to a helmet by a first fastener passing into the at least one substantially axial hole at the second post end and thereby engaging a section of a helmet between the second post end and the first fastener.

16. The retaining post of claim 15, wherein the first fastener is also used to mount the resilient member to the first post end by passing through the substantially axial hole and engaging a second fastener.

17. The retaining post of claim 15, wherein a second fastener is used to mount the resilient member to the first post end.

18. The retaining post of claim 15, wherein the resilient member is a resilient washer.

19. The resilient washer of claim 18, wherein the resilient washer is a serrated washer.

20. The retaining post of claim 15, wherein the retaining post is substantially cylindrical.

21. The retaining post of claim 15, wherein the retaining post is configured to releasably engage the goggle.

22. A goggle system retaining post for attachment to a helmet, the retaining post comprising:
- a substantially cylindrical retaining post having a first post end and a second post end,
- a substantially axial hole passing through the substantially cylindrical retaining post from the first post end to the second post end,
- a resilient serrated washer mounted to the first post end by a first fastener passing through the resilient serrated washer and the substantially axial hole, and
- a second fastener being engagable with the first fastener for securing the retaining post to a helmet at the second post end.

23. The goggle system retaining post of claim 22, wherein the retaining post is configured to releasably engage the goggle.

24. A goggle and goggle mounting system for mounting the goggle to a helmet comprising:
- a goggle;
- a retaining post configured to releasably engage a goggle and having a first post end and a second post end;
- a resilient member mounted on the post body at the first post end;
- the retaining post being directly mountable to a helmet at the second post end; and
- a strap having a first strap end able to attach to the goggle, and a second strap end having an opening therein, the opening being sized to pass interferingly over the resilient member.

25. A helmet and goggle and goggle mounting system comprising:
- a helmet;
- a goggle;
- a retaining post configured to releasably engage a goggle and having a first post end and a second post end;
- a resilient member mounted on the post body at the first post end,
- the retaining post being directly mountable to a helmet at the second post end; and
- a strap having a first strap end able to attach to the goggle, and a second strap end having an opening therein, the opening being sized to pass interferingly over resilient member.

* * * * *